(12) United States Patent
Hirsch

(10) Patent No.: US 9,084,656 B2
(45) Date of Patent: Jul. 21, 2015

(54) DENTAL ASPIRATION DEVICE AND METHOD OF USE

(71) Applicant: Innerlite, Inc., Santa Barbara, CA (US)

(72) Inventor: James A. Hirsch, Santa Barbara, CA (US)

(73) Assignee: Innerlite, Inc., Santa Barbara, CA (US)

( * ) Notice: Subject to any disclaimer, the term of this patent is extended or adjusted under 35 U.S.C. 154(b) by 0 days.

(21) Appl. No.: 14/248,719

(22) Filed: Apr. 9, 2014

(65) Prior Publication Data

US 2014/0308626 A1   Oct. 16, 2014

Related U.S. Application Data

(60) Provisional application No. 61/811,651, filed on Apr. 12, 2013.

(51) Int. Cl.
| | | |
|---|---|---|
| A61C 17/14 | (2006.01) | |
| A61C 17/06 | (2006.01) | |
| A61C 19/00 | (2006.01) | |

(52) U.S. Cl.
CPC .............. *A61C 17/043* (2013.01); *A61C 17/04* (2013.01); *A61C 19/002* (2013.01)

(58) Field of Classification Search
CPC ...... A61C 17/04; A61C 17/16; A61C 17/043; A61C 17/0208; A61C 1/0061; A61C 1/16
USPC ......................................... 433/29, 77, 91–95
See application file for complete search history.

(56) References Cited

U.S. PATENT DOCUMENTS

| | | | | |
|---|---|---|---|---|
| 2,035,585 | A * | 3/1936 | Boeger et al. | 433/93 |
| 3,049,806 | A * | 8/1962 | Cofresi | 433/93 |
| 4,017,975 | A * | 4/1977 | Johnson | 433/94 |
| 4,861,266 | A * | 8/1989 | Ashiku | 433/95 |
| 7,287,981 | B2 | 10/2007 | Hirsch | |
| 2009/0274991 | A1 | 11/2009 | Black | |
| 2010/0129770 | A1* | 5/2010 | Benfield et al. | 433/77 |
| 2012/0015320 | A1 | 1/2012 | Koo | |

FOREIGN PATENT DOCUMENTS

| | | | | |
|---|---|---|---|---|
| JP | 2012075705 | | 4/2012 | |
| WO | WO 2010101407 | A2 * | 9/2010 | A61B 1/24 |
| WO | WO2012051541 | | 4/2012 | |

OTHER PUBLICATIONS

International Search Report and Written Opinion for PCT/US2014/033545, Aug. 8, 2014, 10 pgs.

* cited by examiner

*Primary Examiner* — Cris L Rodriguez
*Assistant Examiner* — Matthew Saunders
(74) *Attorney, Agent, or Firm* — Stephen C. Beuerle; Procopio Cory Hargreaves & Savitch LLP

(57) ABSTRACT

A dental aspiration device includes an inside housing having a proximal portion and a distal portion with an interior surface; an outside housing having a proximal portion and a distal portion with an interior surface; at least one of the interior surfaces of the inside housing and the outside housing including vacuum channels; a hinge connection mechanism hingeably connecting the proximal portions of the inside housing and the outside housing; and a locking mechanism for removably attaching the distal portions of the inside housing and the outside housing to each other.

13 Claims, 9 Drawing Sheets

DENTAL ASPIRATION DEVICE AND METHOD OF USE

CROSS-REFERENCE TO RELATED APPLICATIONS

This application claims priority under 35 U.S.C. 119(e) to U.S. provisional patent application No. 61/811,651, filed on Apr. 12, 2013, which is incorporated by reference herein.

FIELD OF THE INVENTION

The present invention relates to dental aspiration instruments.

BACKGROUND OF THE INVENTION

Dental aspiration instruments have been used in the past during medical and dental procedures to aspirate fluid and other debris from a patient's mouth. With sterilization protocols becoming more stringent, especially in university and hospital dental settings, a need exists for dental aspiration instruments that are easier to clean, autoclave, and/or sterilize because debris accumulates in the vacuum channels of the dental aspiration instruments, leaving hidden areas inside the device free to collect debris and impair function.

SUMMARY OF THE INVENTION

To solve these problems and others, the present invention involves a dental aspiration device attachable to a disposable aspiration/retraction mouthpiece.

Because the dental aspiration device hinges open, the vacuum channels of the dental aspiration device are easier to clean than in the past and also provide quieter suction.

Another aspect of the invention involves a dental aspiration device comprising an inside housing having a proximal portion and a distal portion with an interior surface; an outside housing having a proximal portion and a distal portion with an interior surface; at least one of the interior surfaces of the inside housing and the outside housing including vacuum channels; a hinge connection mechanism hingeably connecting the proximal portions of the inside housing and the outside housing; and a locking mechanism for removably attaching the distal portions of the inside housing and the outside housing to each other.

One or more implementations of the aspect of the invention described immediately above includes one or more of the following: the inside housing is a substantially L-shaped inside housing and the outside housing is a substantially L-shaped outside housing; the locking mechanism includes a locking barb connection mechanism with locking barbs and locking barb receptacles that removably receive the locking barbs, the locking barbs and locking barb receptacles including respective downwardly and rearwardly angled surfaces operatively associated with each other to lock the distal portions together; at least one of the distal portions of the substantially L-shaped inside housing and the substantially L-shaped outside housing includes one or more tangs extending distally therefrom to facilitate separation of the distal portions; the interior surfaces are soft lining overmolds and at least one of the interior surfaces includes compressible sealing ridges between the vacuum channels for sealingly engaging the interior surfaces together; a valve block and at least one of the substantially L-shaped inside housing and the substantially L-shaped outside housing includes a base that receives the valve block; the valve block includes a pair of upper vacuum ports and laterally disposed holes and the base includes laterally disposed holes that align with the laterally disposed holes of the valve block; substantially cylindrical valve members received in the laterally disposed holes, valve controls including levers to control pivotal movement of the valve members in the laterally disposed holes, and holes in the substantially cylindrical valve members to selectively communicate with vacuum channels for controlling aspiration through the vacuum channels; at least one of the distal portions of the substantially L-shaped inside housing and the substantially L-shaped outside housing includes a pair of circular hinge members having holes aligned with the laterally disposed holes for pivotally connecting the substantially L-shaped inside housing and the substantially L-shaped outside housing together; the distal portion of the substantially L-shaped inside housing includes an underside with locking barbs extending therefrom that engage corresponding slots in a connection section of a intraoral device; the valve block includes an additional lateral hole and the base includes at least one additional hole aligned with the additional lateral hole of the valve block, and further including a dowel pin disposed in the additional lateral hole of the valve block and at least one additional hole of the base for securing the base and the valve block together.

A further aspect of the invention involves a method of cleaning the dental aspiration device comprising removing the dowel pin from the additional lateral hole of the valve block and at least one additional hole of the base; removing the substantially cylindrical valve members and valve controls from the laterally disposed holes; separating the valve block from the base; separating the substantially L-shaped outside housing and the substantially L-shaped inside housing from each other; and sterilizing the substantially cylindrical valve members and valve controls, valve block, substantially L-shaped outside housing, and the substantially L-shaped inside housing.

A still further aspect of the invention involves a method of cleaning the dental aspiration device comprising unlocking the distal portions of the outside housing and the inside housing from each other; pivoting and separating the outside housing and the inside housing from each other about the hinge connection mechanism so that the vacuum channels are exposed; and cleaning the vacuum channels.

Another aspect of the invention involves a method of using the dental aspiration device comprising connecting the intraoral device to the dental aspiration device by sliding the connection section of the intraoral device over the distal portion of the dental aspiration device and engaging the slots in the connection section of the intraoral aspiration device with the locking barbs of the distal portion of the dental aspiration device; connecting the dental aspiration device to a suction hose; inserting the intraoral device into the mouth of a patient; and aspirating fluids from the patient's mouth using the intraoral device and the dental aspiration device.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION OF PREFERRED EMBODIMENTS

Figure 1:
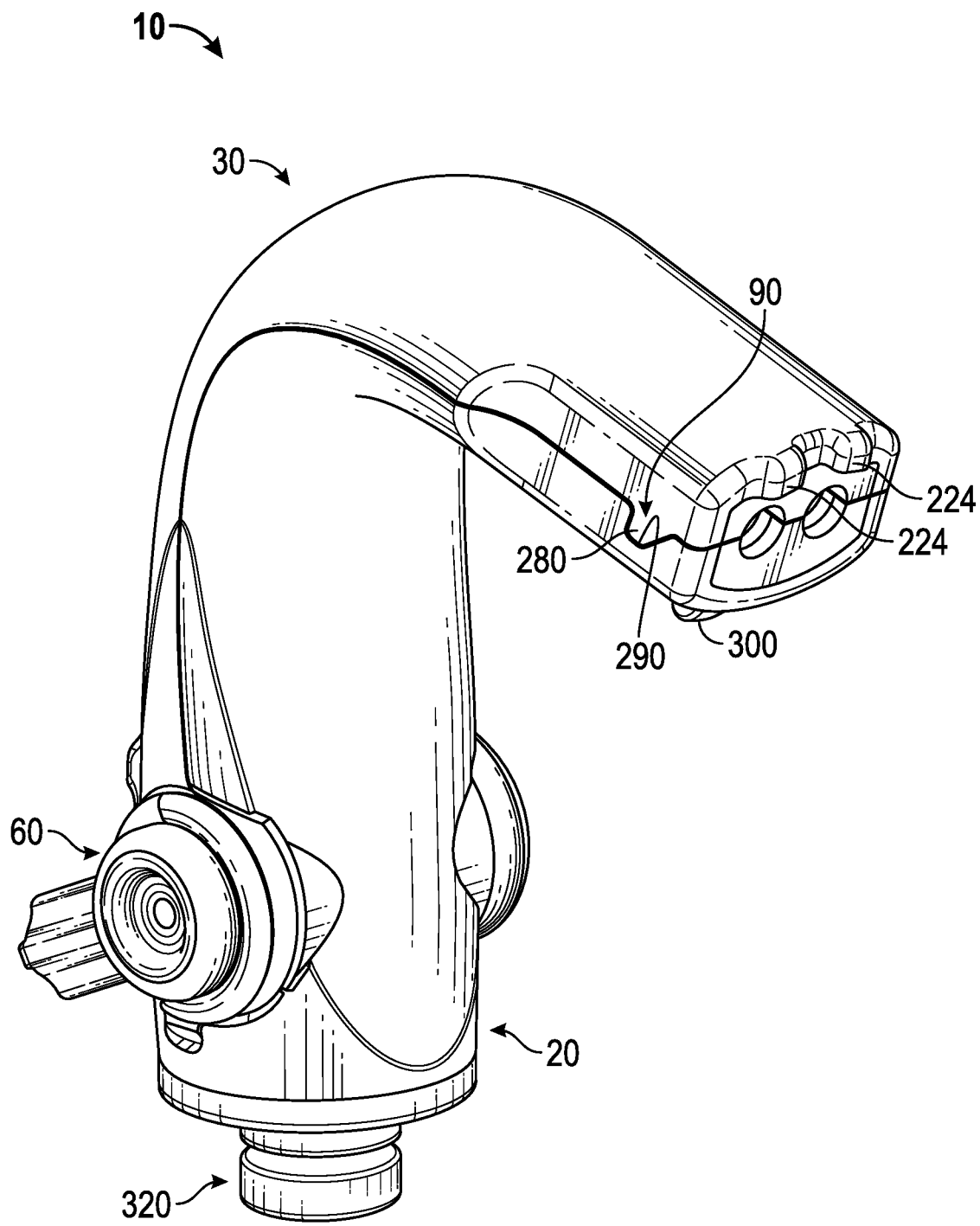
FIG. 1 is a perspective view of an embodiment of a dental aspiration device.
Figure 2:
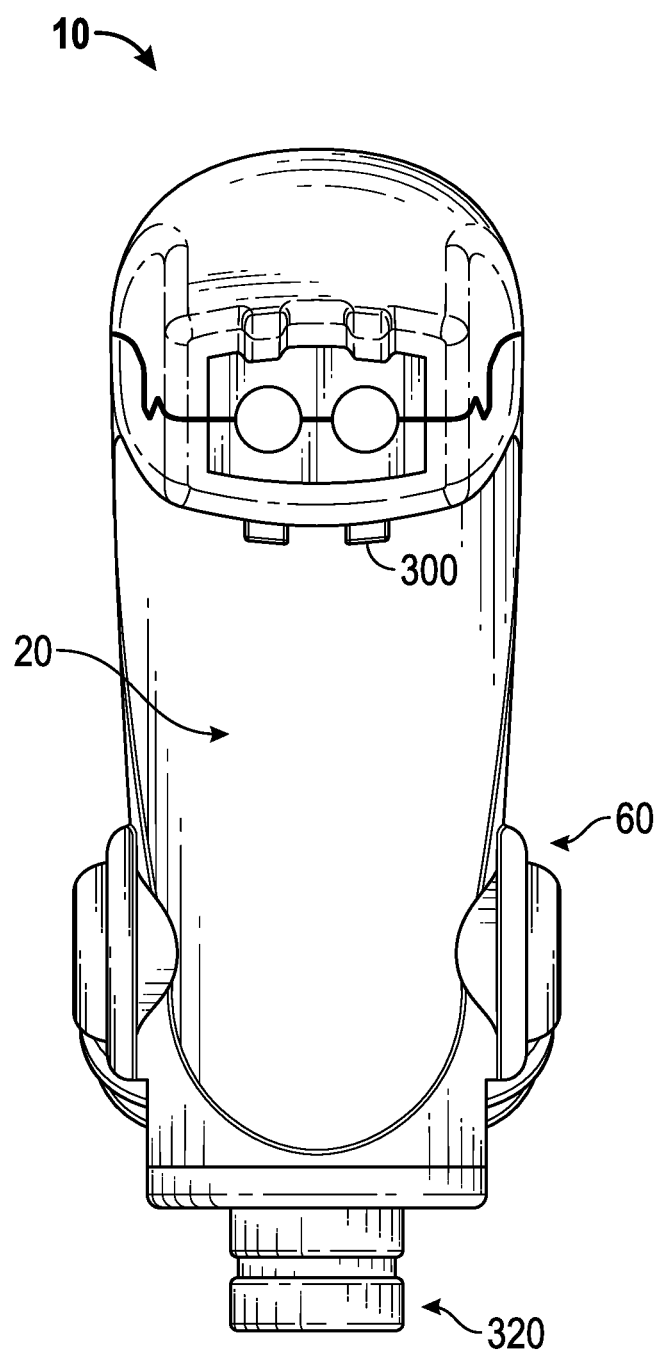
FIG. 2 is a front view of the dental aspiration device.
Figure 3:
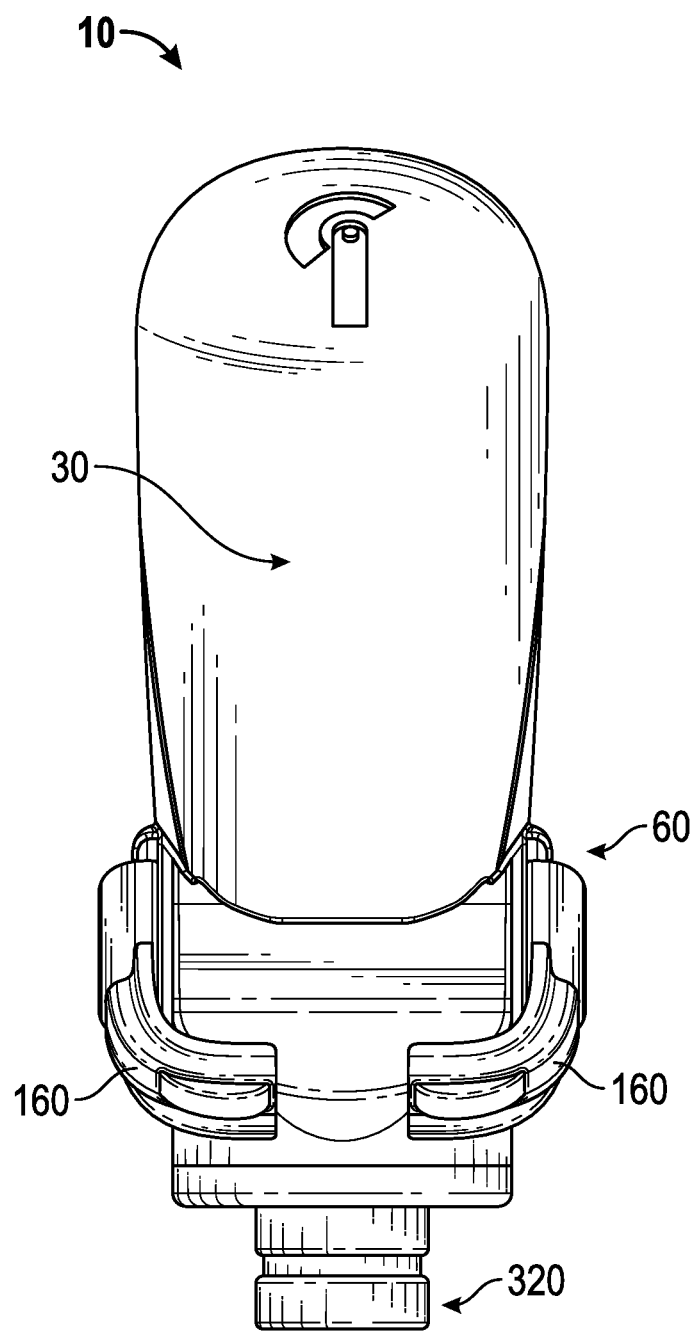
FIG. 3 is a back view elevational view of the dental aspiration device.

With reference to FIGS. 1-9, an embodiment of a dental aspiration device 10 and method of using and cleaning the same will be described. The dental aspiration device 10 includes a substantially L-shaped inside housing 20 and a substantially L-shaped outside housing 30 hingeably connected to each other at proximal portions 40, 50 via a hinge connection mechanism 60 and removably attachable to each other at distal portions 70, 80 via a locking barb connection mechanism 90.

The inside housing 20 includes a base 100 that receives a valve block 110. The valve block 110 includes a pair of upper vacuum ports 111 and a laterally disposed hole 112 (aligned with laterally disposed holes 114, 116, 117 of base 100) that pivotally receives substantially cylindrical valve members 120 and friction and sealing O-rings 122, 123 of valve members 120 of valve controls 140, 150. The valve controls 140, 150 include levers 160 to control pivotal movement of the valve members 120. The valve members 120 include respective holes 170 to selectively communicate with vacuum channels 180, 190 for controlling aspiration through the vacuum channels 180. The valve block 110 and the base 100 include respective holes 202, 210 that receive a dowel pin 220 for connecting the valve block 110 within the base 100. The valve block 110 includes a vacuum tube connector 320 that attaches to an existing office suction hose 310.

The outside housing 30 includes a pair of circular hinge members 222 that define holes 116 aligned with the holes 112, 114 for pivotally connecting the outside housing 30 to the inner housing 20. At the distal portion of the outside housing 30, a pair of tangs 224 extend therefrom to allow a user to separate, lift, and pivot the outside housing 30 relative to the inner housing 20 to an open configuration.

The vacuum channels 180, 190 are formed in soft lining overmolds 230, 240 carried within the inside housing 20 and the outside housing 30. One or both of the overmolds 230, 240 include compressible sealing ridges 250, 260, 270 that sealingly engage each other when the inside housing 20 and the outside housing 30 are closed together. A central sealing ridge 260 has a raised sealing surface.

Figure 4:
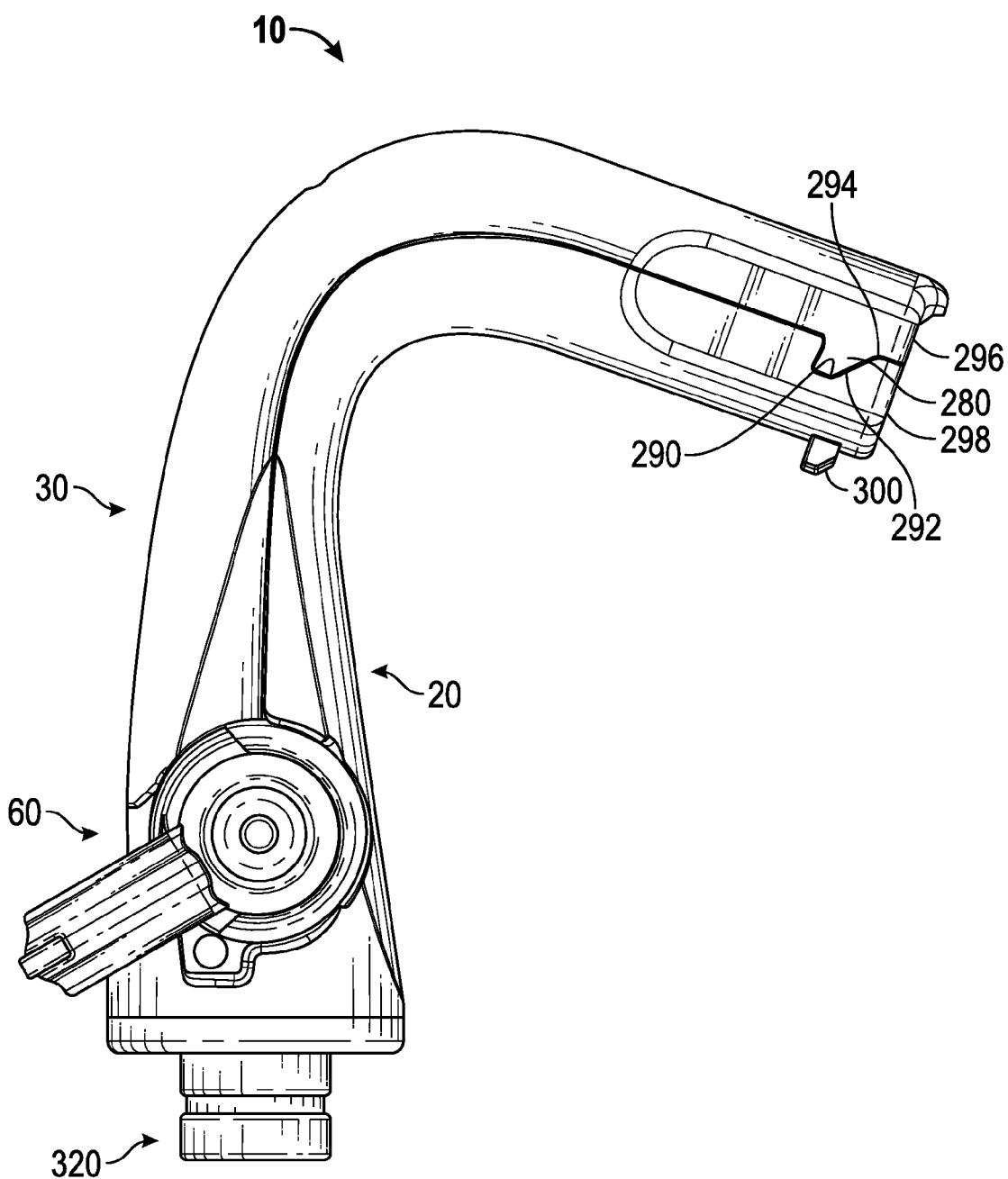
FIG. 4 is right elevational view of the dental aspiration device.
Figure 5:
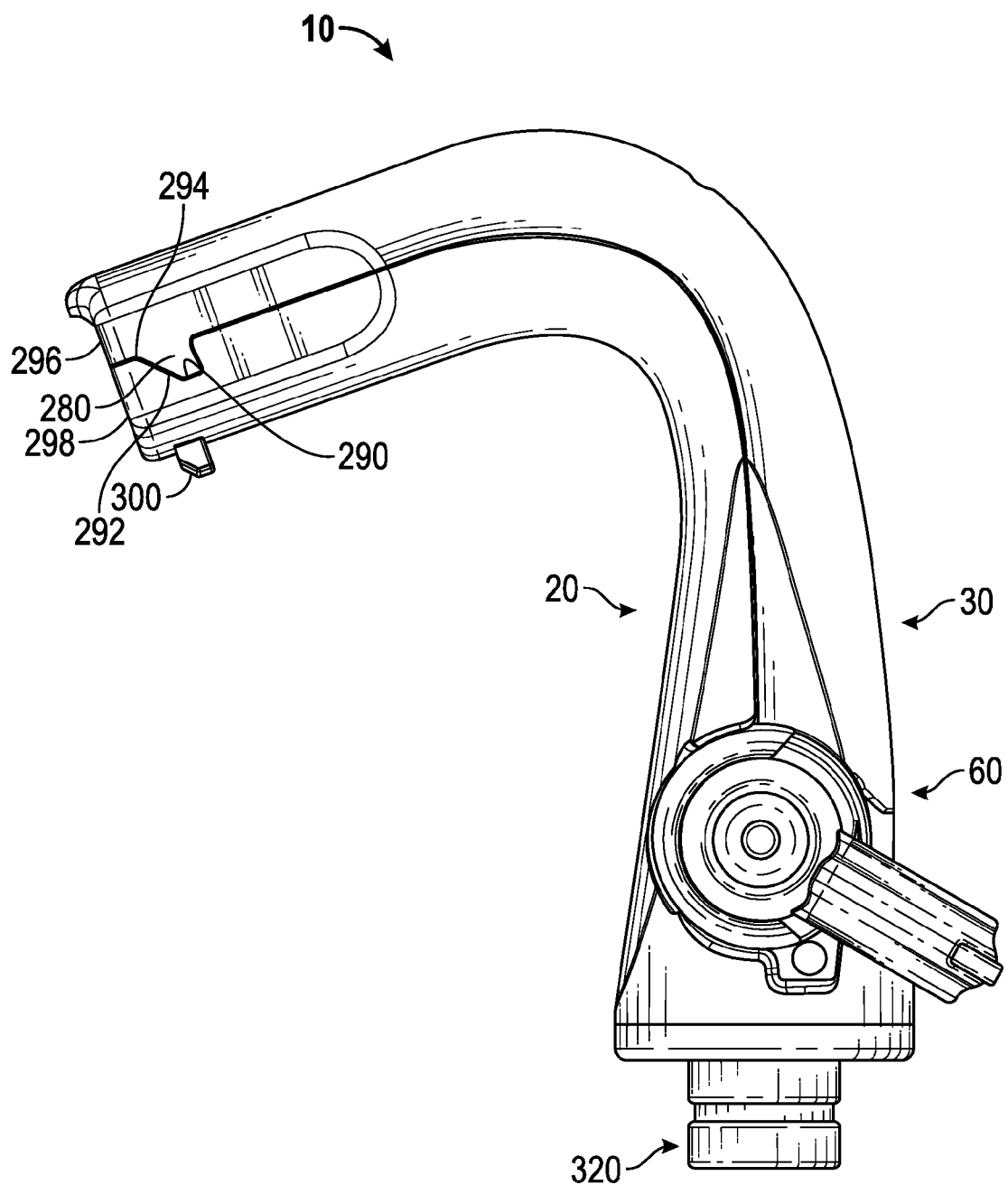
FIG. 5 is a left elevational view of the dental aspiration device.
Figure 7:
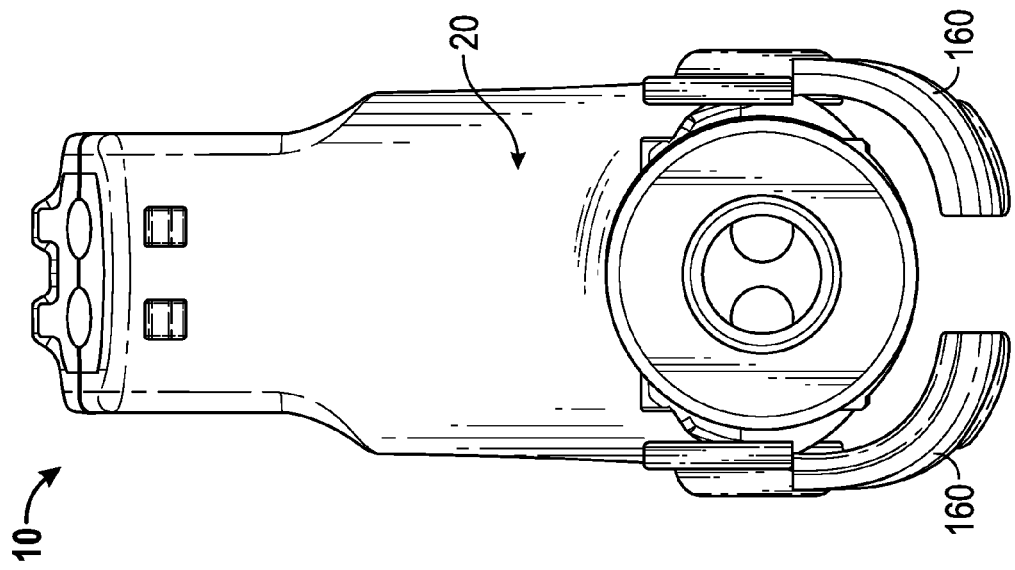
FIG. 7 is a bottom plan view of the dental aspiration device.
Figure 6:
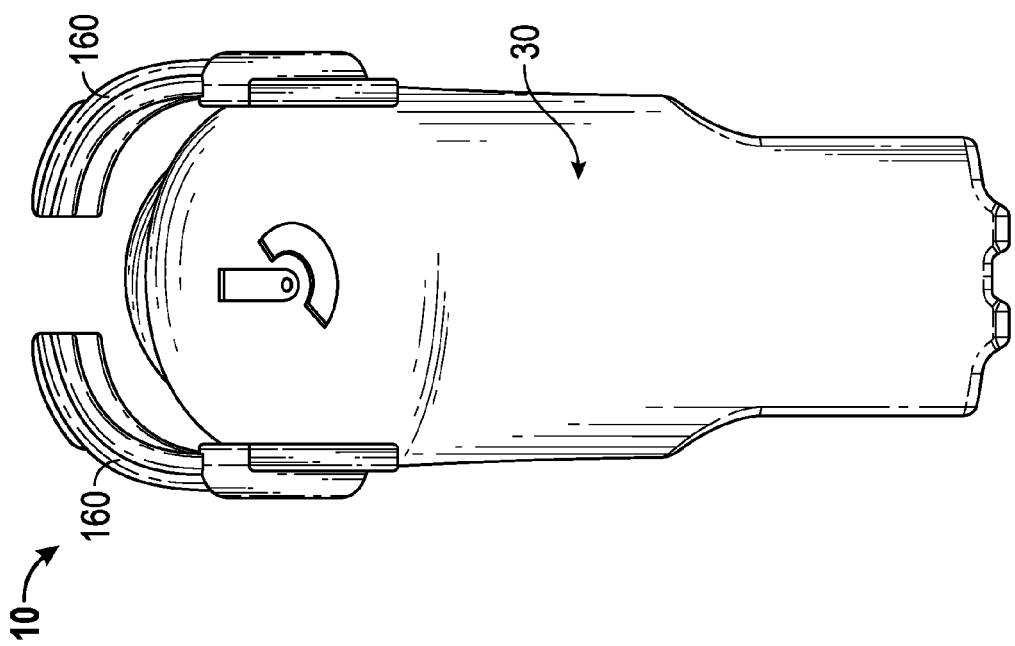
FIG. 6 is a top plan view of the dental aspiration device.
Figure 8:
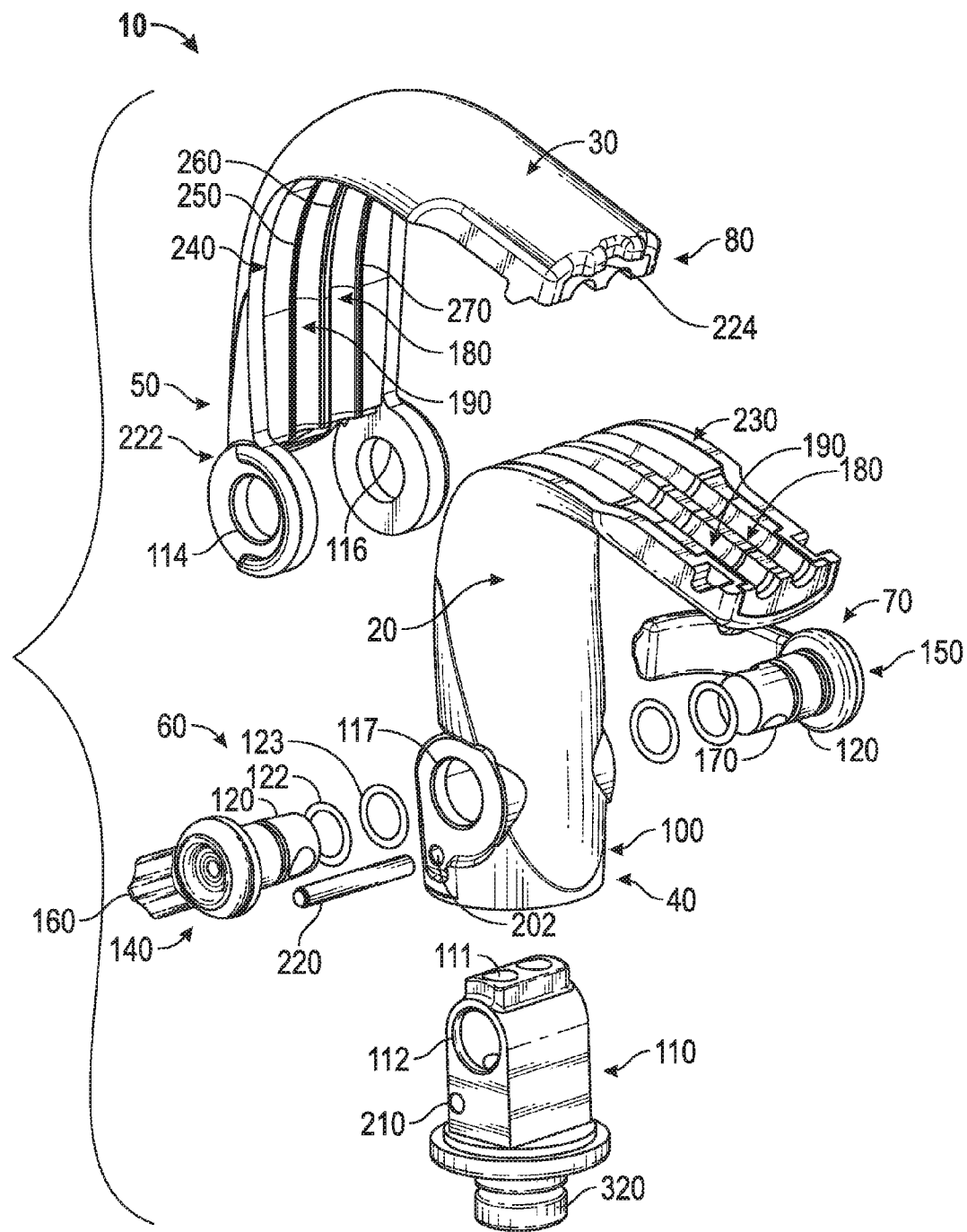
FIG. 8 is an exploded perspective view of the dental aspiration device.
Figure 9:
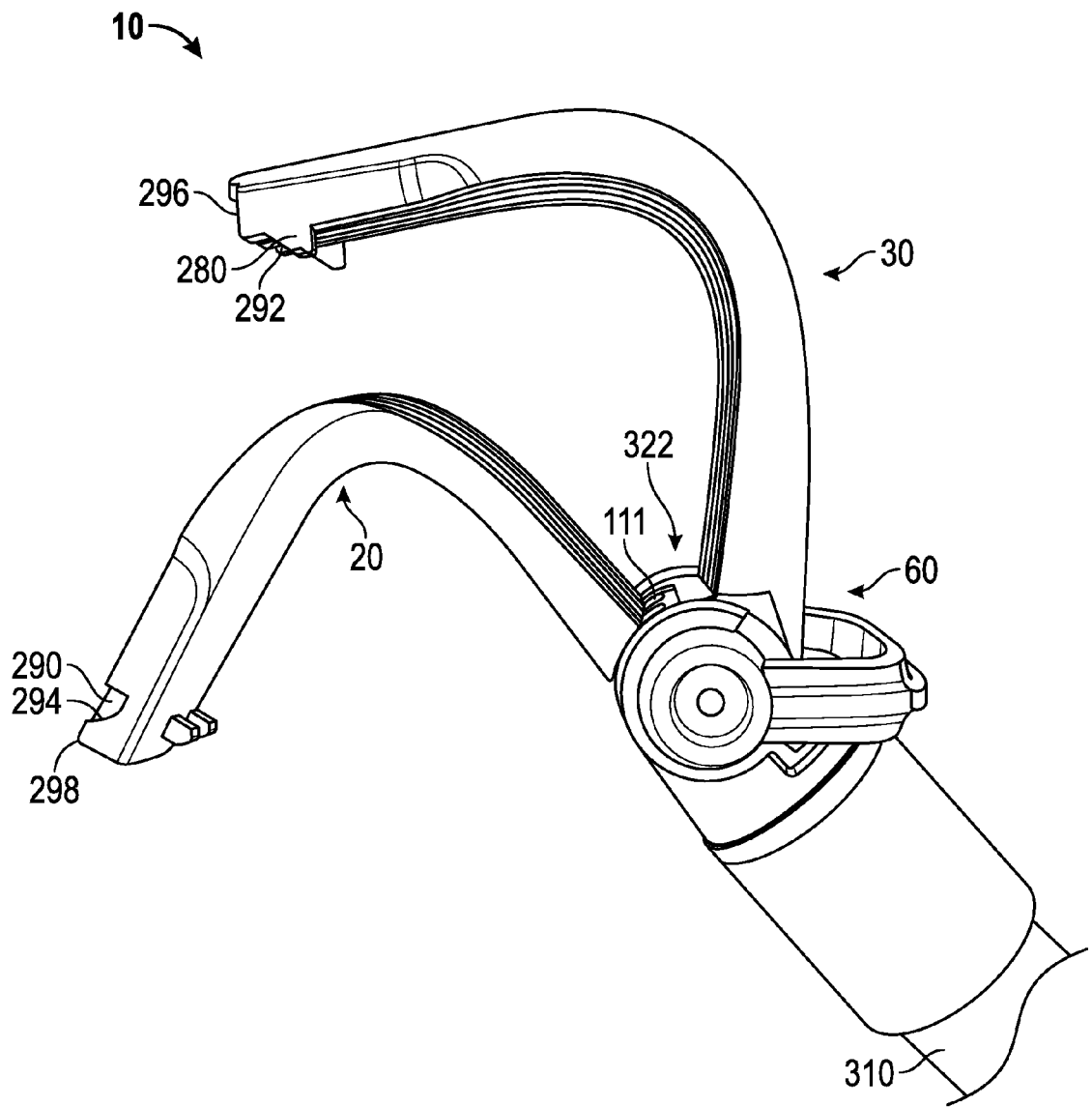
FIG. 9 is a perspective view of the dental aspiration device showing the inside housing and the outside housing of the dental aspiration device hinged to an open configuration.

The locking barb connection mechanism 90 includes locking barbs 280 that detachably connect to locking barb receptacles 290 for detachably connecting the distal portions 70, 80 of the inside housing 20 and the outside housing 30 together. As shown in FIGS. 4, 5, and 9, the locking barbs 280 and locking barb receptacles 292 include respective rearwardly angled surfaces 292, 294 that slope downward and rearward from distal tips 296, 298 of the outside housing 30 and the inside housing 20, towards hinge connection mechanism 60. To lock the distal portions 70, 80 together, the outside housing 30 is pivoted relative to the inner housing 20 about hinge connection mechanism 60 to the closed configuration shown in FIGS. 4 and 5. The rearwardly angled surface 292 of the outside housing 30 contacts and slides down the rearwardly angled surface 294 of the inside housing 20, drawing the distal portions 70, 80 together into the closed and locked configuration shown in FIGS. 4 and 5.

Figure 10:
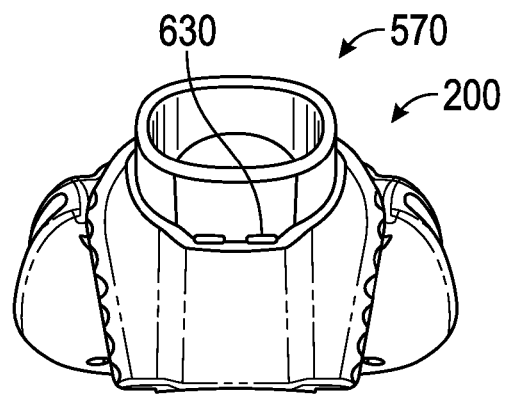
FIG. 10 is a right side elevational of an embodiment of an intraoral illumination device used with the dental aspiration device to form a dental aspiration assembly.
Figure 11:
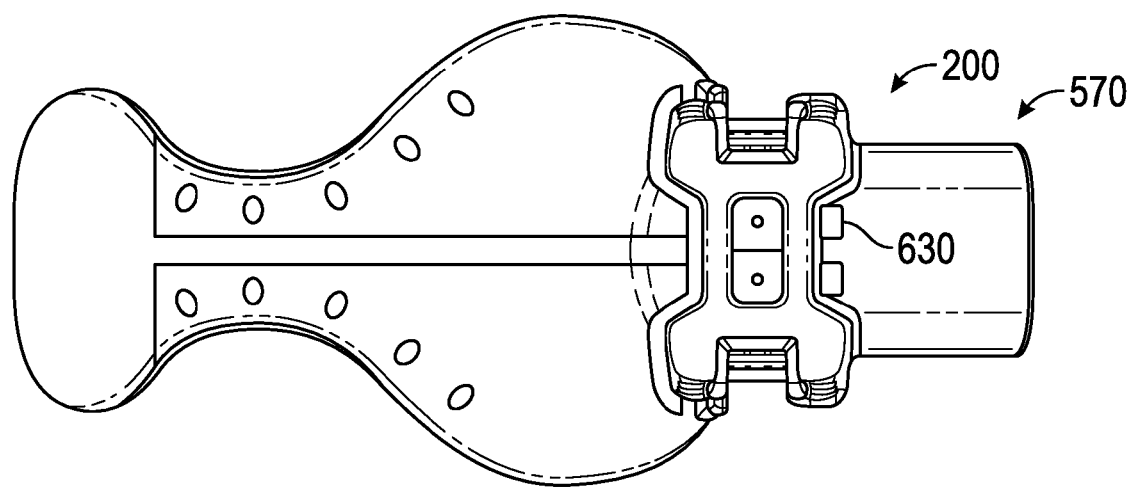
FIG. 11 is a rear elevational view of the intraoral illumination device illustrated in FIG. 10.

With reference additionally to FIGS. 10 and 11, an underside of the distal portion 70 of the inside housing 20 includes locking barbs 300 that engage corresponding slots 630 in connection section 570 to retain the dental aspiration device 10 in the connection section 570 of disposable intraoral device or aspiration/retraction mouthpiece 200. Together, the dental aspiration device 10 and the connected intraoral device 200 form a dental aspiration assembly.

An exemplary method of using the dental aspiration device 10 includes connecting the intraoral device 200 to the dental aspiration device 10 by sliding the connection section 570 of the intraoral device 200 over the distal portion of the dental aspiration device 10 and engaging the slots 630 in the connection section 570 of the intraoral aspiration device 10 with the locking barbs 300 of the distal portion of the dental aspiration device 10; connecting the dental aspiration device 10 to suction hose 310; inserting the intraoral device 200 into the mouth of a patient; and aspirating fluids from the patient's mouth using the intraoral device 200 and the dental aspiration device 10.

The vacuum channels 180, 190 communicate with vacuum channels in the intraoral device 200 for aspirating fluid from a patient's mouth through the dental aspiration device 10 and the suction hose 310 attached to the vacuum tube connector 320 of valve block 110. Control of the levers 160 causes the valve controls 140, 150 to respectively control the vacuum force through the vacuum channels in the intraoral device 200.

With reference to FIG. 9, to prevent leaking in the hinge connection mechanism 60 of the dental aspiration device 10, proud surface at hinge point 322 seals around upper vacuum ports 111 when the dental aspiration device 10 is in the closed configuration.

To clean the soft lining overmolds 230, 240 of the vacuum channels 180, 190, a user unlocks the locking barb connection mechanism 90 at the distal portions 70, 80 by using the pair of tangs 224 to separate and pivot the distal portions 70, 80 from each other and pivot the outside housing 30 relative to the inner housing 20 to the open configuration shown in FIG. 9. In the open configuration, the vacuum channels 180, 190 of the dental aspiration device 10 are exposed and easily accessible for cleaning.

The dental aspiration device 10 may also be easily disassembled for sterilization/autoclaving, or other purposes by removing the valve controls 140, 150, removing the dowel pin 220 (dowel pin 220 only removed for repair, not cleaning), and separating the valve block 110, the inner housing 20, and the outside housing 30 from each other so that all the components can be cleaned/sterilized/autoclaved.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in any following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

I claim:

1. A dental aspiration device, comprising:
   an inside housing having a proximal portion and a distal portion with an interior surface;
   an outside housing having a proximal portion and a distal portion with an interior surface;
   at least one of the interior surfaces of the inside housing and the outside housing including vacuum channels;
   a hinge connection mechanism hingeably connecting the proximal portions of the inside housing and the outside housing; and
   a locking mechanism for removably attaching the distal portions of the inside housing and the outside housing to each other,
   wherein the inside housing is a substantially L-shaped inside housing and the outside housing is a substantially L-shaped outside housing.

2. The dental aspiration device of claim 1, wherein the locking mechanism includes a locking barb connection mechanism with locking barbs and locking barb receptacles that removably receive the locking barbs, the locking barbs and locking barb receptacles including respective downwardly and rearwardly angled surfaces operatively associated with each other to lock the distal portions together.

3. The dental aspiration device of claim 1, wherein at least one of the distal portions of the substantially L-shaped inside housing and the substantially L-shaped outside housing includes one or more tangs extending distally therefrom to facilitate separation of the distal portions.

4. The dental aspiration device of claim 1, wherein the interior surfaces are soft lining overmolds and at least one of the interior surfaces includes compressible sealing ridges between the vacuum channels for sealingly engaging the interior surfaces together.

5. The dental aspiration device of claim 1, further including a valve block and at least one of the substantially L-shaped inside housing and the substantially L-shaped outside housing includes a base that receives the valve block.

6. The dental aspiration device of claim 5, wherein the valve block includes a pair of upper vacuum ports and laterally disposed holes and the base includes laterally disposed holes that align with the laterally disposed holes of the valve block.

7. The dental aspiration device of claim 6, further including substantially cylindrical valve members received in the laterally disposed holes, valve controls including levers to control pivotal movement of the valve members in the laterally disposed holes, and holes in the substantially cylindrical valve members to selectively communicate with vacuum channels for controlling aspiration through the vacuum channels.

8. The dental aspiration device of claim 7, wherein at least one of the distal portions of the substantially L-shaped inside housing and the substantially L-shaped outside housing includes a pair of circular hinge members having holes aligned with the laterally disposed holes for pivotally connecting the substantially L-shaped inside housing and the substantially L-shaped outside housing together.

9. The dental aspiration device of claim 1, wherein the distal portion of the substantially L-shaped inside housing includes an underside with locking barbs extending therefrom.

10. The dental aspiration device of claim 5, wherein the valve block includes an additional lateral hole and the base includes at least one additional hole aligned with the additional lateral hole of the valve block, and further including a dowel pin disposed in the additional lateral hole of the valve block and at least one additional hole of the base for securing the base and the valve block together.

11. A method of cleaning the dental aspiration device of claim 10, comprising:
   removing the dowel pin from the additional lateral hole of the valve block and at least one additional hole of the base;
   removing the substantially cylindrical valve members and valve controls from the laterally disposed holes;
   separating the valve block from the base;
   separating the substantially L-shaped outside housing and the substantially L-shaped inside housing from each other;
   sterilizing the substantially cylindrical valve members and valve controls, valve block, substantially L-shaped outside housing, and the substantially L-shaped inside housing.

12. A method of cleaning the dental aspiration device of claim 1, comprising:
   unlocking the distal portions of the outside housing and the inside housing from each other;
   pivoting and separating the outside housing and the inside housing from each other about the hinge connection mechanism so that the vacuum channels are exposed;
   cleaning the vacuum channels.

13. A method of using the dental aspiration device of claim 9, comprising:

connecting an intraoral device including a connection section with slots to the dental aspiration device by sliding the connection section of the intraoral device over the distal portion of the dental aspiration device and engaging the slots in the connection section of the intraoral aspiration device with the locking barbs of the distal portion of the dental aspiration device;
connecting the dental aspiration device to a suction hose;
inserting the intraoral device into the mouth of a patient;
aspirating fluids from the patient's mouth using the intraoral device and the dental aspiration device.

* * * * *